United States Patent
Kotoulas et al.

(10) Patent No.: US 10,783,154 B2
(45) Date of Patent: Sep. 22, 2020

(54) TRANSPOSING OF RANKING MODELS

(71) Applicant: International Business Machines Corporation, Armonk, NY (US)

(72) Inventors: Spyros Kotoulas, Dublin (IE); Natasha Mulligan, Dublin (IE); Marco Luca Sbodio, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 411 days.

(21) Appl. No.: 15/720,123

(22) Filed: Sep. 29, 2017

(65) Prior Publication Data

US 2019/0102394 A1    Apr. 4, 2019

(51) Int. Cl.
| | |
|---|---|
| *G16H 10/60* | (2018.01) |
| *G06F 16/2457* | (2019.01) |
| *G06Q 50/24* | (2012.01) |
| *G06F 16/84* | (2019.01) |
| *G06Q 50/22* | (2018.01) |
| *H04L 29/08* | (2006.01) |

(52) U.S. Cl.
CPC ........ *G06F 16/24578* (2019.01); *G06F 16/86* (2019.01); *G06Q 50/22* (2013.01); *G06Q 50/24* (2013.01); *H04L 67/306* (2013.01)

(58) Field of Classification Search
CPC .................................................. G16H 10/60
See application file for complete search history.

(56) References Cited

U.S. PATENT DOCUMENTS

| | | | |
|---|---|---|---|
| 9,082,086 | B2 | 7/2015 | Kalai et al. |
| 9,179,061 | B1 * | 11/2015 | Kraft ........................ G06T 15/08 |
| 9,268,851 | B2 | 2/2016 | Lin et al. |

(Continued)

FOREIGN PATENT DOCUMENTS

JP          2012123566 A       6/2012

OTHER PUBLICATIONS

Chrisment, M., "Transposing Model Objects in the Relational Context", Feb. 2012, , pp. 23.

(Continued)

*Primary Examiner* — John A Pauls
(74) *Attorney, Agent, or Firm* — Andrew Aubert (57) ABSTRACT

Aspects of the present invention disclose a method, computer program product, and system for transposing ranking models. The method includes computer processors determining an initial ranking modeling framework for a record based on analyzing data from a plurality of sources. The record includes a plurality of objects and an object includes at least one feature. The method further includes computer processors determining a mapping of relationships between features included in the record. The method further includes computer processors identifying a user selection of a feature. The method further includes computer processors determining a transposition path between the user selected feature and a set of features having a determined mapped relationship to the user selected feature. The method further includes computer processors modifying ranking information associated with features included in the determined transposition path. The method further includes computer processors reordering the record based on the modified ranking information.

14 Claims, 6 Drawing Sheets

(56) References Cited

U.S. PATENT DOCUMENTS

| | | |
|---|---|---|
| 9,582,786 B2 | 2/2017 | Gubin et al. |
| 2009/0033664 A1* | 2/2009 | Hao ..................... G06T 11/206 |
| | | 345/440 |
| 2014/0344241 A1 | 11/2014 | Hong |
| 2016/0042052 A1 | 2/2016 | Fitzgerald Groenen et al. |
| 2016/0063202 A1 | 3/2016 | Nandabalan |

OTHER PUBLICATIONS

Guo, et al., "Self-organizing fuzzy aggregation models to rank the objects with multiple attributes", Sep. 2000, pp. 573-580, IEEE Transactions on Systems Man and Cybernatics Part A—Systems and Humans, vol. 30, No. 5.

* cited by examiner

INFORMATION FOR HYPOTHETICAL PATIENT

USER SELECTS "DIABETES" AS AN IMPORTANT PIECE OF INFORMATION FOR THE PATIENT

| CONDITIONS |
|---|
| DEMENTIA |
| HAY FEVER |
| THYROID |
| DIABETES ★ |
| ARTHRITIS |

310

307 → DIABETES

| MEDICATIONS |
|---|
| A |
| B |
| C |
| D |
| E |

320

| ACTIONS |
|---|
| PHYSIO FOR ARTHRITIS |
| IMPROVE MEDICATION ADHERENCE |
| GET EDUCATION ON DIABETES |
| YEARLY CHECKUP FOR THYROID FUNCTION |
| INCREASE PHYSICAL ACTIVITY |

330

| CARE TEAM |
|---|
| DR Y. (ENDOCRINOLOGIST) |
| DR X. (NEUROLOGIST) |
| DR Z. (GENERAL PRACTITIONER) |

TRANSPOSING OF RANKING MODELS

BACKGROUND

The present invention relates generally to the field of information processing and more particularly to Informatics.

Health information technology (HIT) is "the application of information processing involving both computer hardware and software that deals with the storage, retrieval, sharing, and use of health care information, data, and knowledge for communication and decision making." For HIT, technology represents computers and communications attributes that can be networked to build systems for moving health information. Informatics is yet another integral aspect of HIT.

Health informatics refers to the intersection of information science, computer science, and health care. Health informatics describes the use and sharing of information within the healthcare industry with contributions from computer science, mathematics, and psychology. It deals with the resources, devices, and methods required for optimizing the acquisition, storage, retrieval, and use of information in health and biomedicine. Health informatics tools include not only computers but also clinical guidelines, formal medical terminologies, and information and communication systems. Clinical informatics is a sub-discipline that informs health informatics from different disciplinary perspective.

Clinical informatics is concerned with the use of information in health care by and for clinicians. Clinical informaticians, also known as clinical informaticists, transform health care by analyzing, designing, implementing, and evaluating information and communication systems that enhance individual and population health outcomes, improve [patient] care, and strengthen the clinician-patient relationship. Clinical informaticians use their knowledge of patient care combined with their understanding of informatics concepts, methods, and health informatics tools to assess information and knowledge needs of health care professionals and patients, characterize, evaluate, and refine clinical processes.

Clinicians collaborate with other health care and information technology professionals to develop health informatics tools which promote patient care that is safe, efficient, effective, timely, patient-centered, and equitable.

SUMMARY

According to one embodiment of the present invention, a method for transposing ranking models across two or more sets of objects characterized by different features is provided. The method for transposing ranking models across two or more sets of objects characterized by different features may include one or more processors determining an initial ranking modeling framework for a record based on analyzing data from a plurality of sources, wherein the record includes a plurality of objects, and wherein an object includes at least one feature. The method further includes determining a mapping of relationships between features included in the record. The method further includes identifying a user selection of a feature. The method further includes determining a transposition path between the user selected feature and a set of features that have a determined mapped relationship to the user selected feature. The method further includes modifying ranking information associated with features included in the determined transposition path. The method further includes reordering the record based on the modified ranking information.

DETAILED DESCRIPTION

Embodiments of the present invention recognize that users need to work with large amounts of information of differing types. For example, a care worker would need to understand different medications, conditions, goals, barriers, and social determinants that affect the care of a patient. Users have a need to understand what information is more important for a particular case and for themselves.

Embodiments of the present invention recognize that current approaches to determine the relevance of information rely on user feedback on each particular type of information. Additional embodiments of the present invention recognize that current approaches use unified models that statistically tie different information together. Embodiments of the present invention recognize that unified models that rely on statistical relations for consolidating and accurately presenting large amounts of information can rely on training data and relational databases which cannot process unstructured information. A relational database, relying on a unified model, cannot express relationships of parts to sub parts and sub-sub parts.

Embodiments of the present invention provide a method that solicits feedback from an expert user regarding the relevance of a piece of information of a given type and infers the relevance of information of a different type and associated relationships to other information. The system can work with less feedback from users because the present invention can enable the construction of a ranking model for a set of objects using implicit knowledge derived from another ranking model built for other objects. Embodiments of the present invention provide an interactive algorithm that employs feedback driven measurements and data to enable statistical analysis in typically intractable situations. Embodiments of the present invention use interactive data acquisition tools to facilitate statistically and computationally efficient learning algorithms that are suited to create connections in non-uniform datasets. Embodiments of the present invention are well suited to create connections and capture the important aspects of non-uniform datasets.

Figure 1:
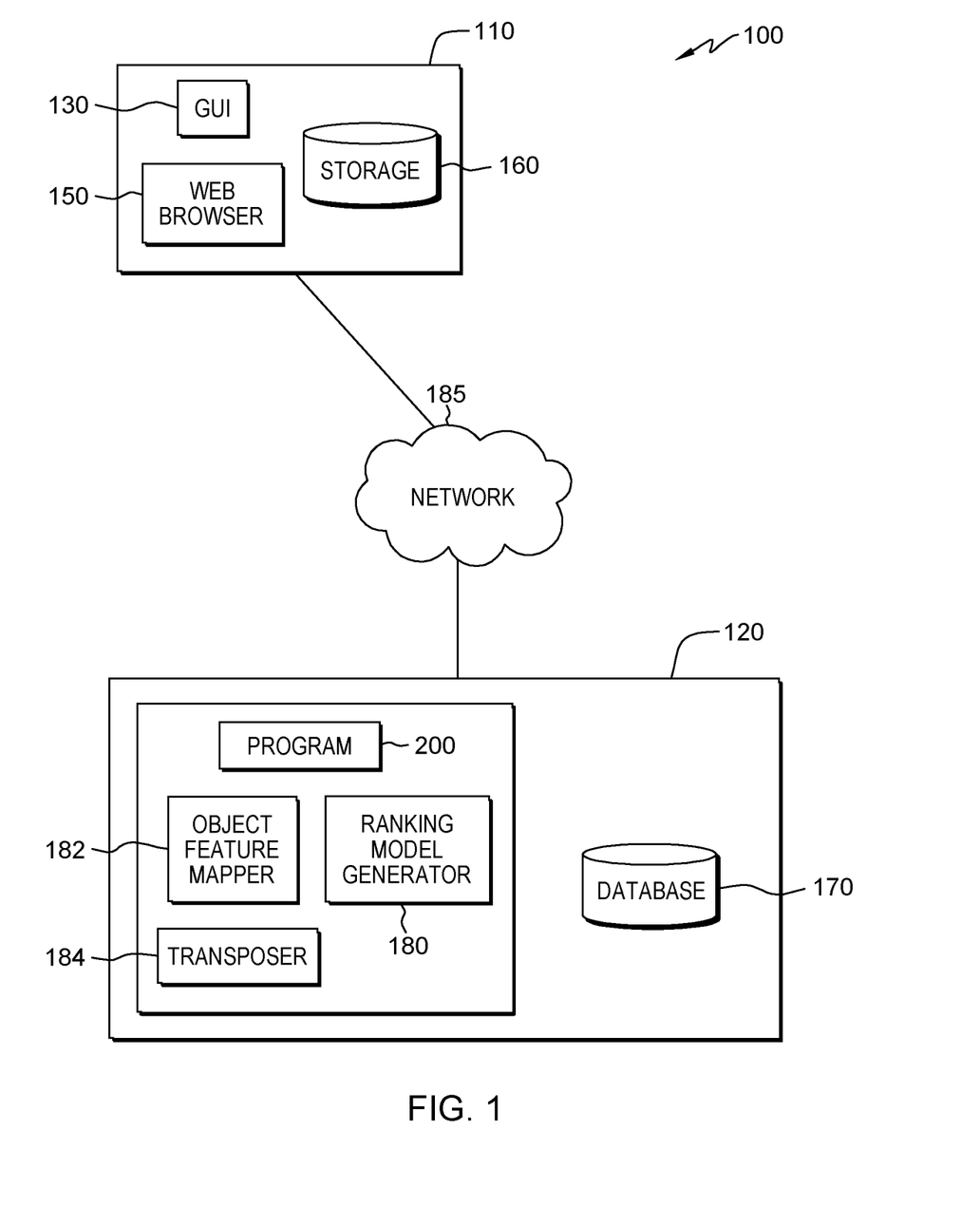
FIG. 1 is a functional block diagram illustrating a distributed data processing environment, in accordance with an embodiment of the present invention.

Example embodiments, in accordance with the present invention, will now be described in detail with reference to the Figures. FIG. 1 is a functional block diagram, illustrating distributed data processing environment 100. Distributed data processing environment 100 includes computing device 110, server computer 120, interconnected over network 185.

In one embodiment, computing device 110 includes graphical user interface (GUI) 130, web browser 150, and storage 160. The various programs on computing device 110 include a web browser, an electronic mail client, security software (e.g., a firewall program, a geo-locating program, an encryption program, etc.), an instant messaging (IM) application (app), and a communication (e.g., phone) application.

Computing device 110 may be a desktop computer, a laptop computer, a tablet computer, a specialized computer server, a smartphone, a wearable device (e.g., smart watch, personal fitness device, personal safety device), or any programmable computer system known in the art with an interactive display or any other computer system known in the art. In certain embodiments, computing device 110 represents a computer system utilizing clustered computers and components that act as a single pool of seamless resources when accessed through network 185, as is common in data centers and with cloud computing applications. In general, computing device 110 is representative of any programmable electronic device or combination of programmable electronic devices capable of executing machine-readable program instructions and communicating with other computer devices via a network.

In one embodiment, graphical user interface 130 operates on computing device 110. In another embodiment, graphical user interface 130 operates on another computer in a server-based setting; for example, on a server computer (e.g., server computer 120). In yet another embodiment, graphical user interface 130 operates on computing device 110 simultaneously with a server computer interconnected through network 185 (e.g., server computer 120). Graphical user interface 130 may be any user interface used to access information from computing device 110, such as information gathered or produced by program 200. Additionally, graphical user interface 130 may be any user interface used to supply information to computing device 110, such as information supplied by a user to be used by program 200. In some embodiments, graphical user interface 130 may present a generic web browser used to retrieve, present, and negotiate resources from the Internet. In other embodiments, graphical user interface 130 may be a software or application that enables a user at computing device 110 access to network 185.

In yet another embodiment, a user of computing device 110 can interact with graphical user interface 130 through a touch screen that performs as both an input device to a graphical user interface (GUI) and as an output device (i.e., an electronic display) presenting a plurality of icons associated with software applications or images depicting the executing software application. Optionally, a software application (e.g., a web browser) can generate graphical user interface 130 operating within the GUI of computing device 110. Graphical user interface 130 accepts input from a plurality of input/output (I/O) devices including, but not limited to, a tactile sensor interface (e.g., a touch screen or a touchpad) referred to as a multi-touch display. An I/O device interfacing with graphical user interface 130 may be connected to computing device 110, which may operate utilizing wired (e.g., USB port) or wireless network communications (e.g., infrared, NFC, etc.). Computing device 110 may include components, as depicted and described in further detail with respect to FIG. 3, in accordance with embodiments of the present invention.

Web browser 150 may be a generic web browser used to retrieve, present, and traverse information resources from the Internet. In some embodiments, web browser 150 may be a web browser designed for a mobile device. In other embodiments, web browser 150 may be a web browser designed for a traditional computing device, such as a desktop computer, PC, or laptop. In general, web browser 150 may be any application or software that enables a user of computing device 110 to access a webpage over network 185. In the depicted environment, web browser 150 resides on computing device 110. In other embodiments, web browser 150, or similar web browsers, may reside on other computing devices capable of accessing a webpage over network 185.

Storage 160 (e.g., a database) located on computing device 110, represents any type of storage device capable of storing data that is accessed and utilized by computing device 110. In other embodiments, storage 160 represents multiple storage devices within computing device 110. Storage 160 stores information, such as, but not limited to, account information, credentials for authentication, user preferences, lists of preferred users, previously visited websites, history of visited Wi-Fi portals, and the history of the location of the computing device.

In general, network 185 can be any combination of connections and protocols that will support communications among computing device 110. Network 185 can include, for example, a local area network (LAN), a wide area network (WAN), such as the Internet, a cellular network, or any combination of the preceding, and can further include wired, wireless, and/or fiber optic connections.

Server computer 120 may be a desktop computer, a laptop computer, a tablet computer, a specialized computer server, a smartphone, or any other computer system known in the art. In certain embodiments, server 120 represents a computer system utilizing clustered computers and components that act as a single pool of seamless resources when accessed through network 185, as is common in data centers and with cloud computing applications. In general, server computer 120 is representative of any programmable electronic device or combination of programmable electronic devices capable of executing machine-readable program instructions and communicating with other computer devices via a network. In one embodiment, server computer 120 includes database 170, ranking model generator 180, object feature mapper 182, transposer 184, and program 200.

In an embodiment, server 120 is capable of initiating a handshake process between server computer 120 and computing device 110. Handshaking is an automated process of negotiation that dynamically sets parameters of a communications channel established between two entities before normal communication over the channel begins. Handshaking follows the physical establishment of the channel and precedes normal information transfer. Handshaking facilitates connecting heterogeneous computing systems, or equipment, over a communication channel without the need for user intervention to set parameters. In an example, server computer 120 initiates the handshake process by sending a message to computing device 110 indicating that server computer 120 wants to establish a communication channel in order to gain access to programs on computing device 110.

Ranking model generator 180 (a sub program of program 200) generates a ranking model for a set of objects, O1, characterized by the set of features F1. In an embodiment, ranking model generator 180 constructs a ranking model for a set of objects using implicit knowledge derived from another ranking model built for another set of objects. In an example, ranking model generator 180 generates a ranking model for O1 based on F1. Ranking model generator 180 accesses database 170 to determine the history of the importance of an item of data and uses user preferences to determine the importance of an item of data and adapts the new ranking model with this data.

Object feature mapper 182 (a sub program of program 200) analyzes a feature space and determines a mapping among values of one or more features in a first set of features, F1, to values of one or more features in a second set or features, F2. In an embodiment, F1 are features that characterize a first set of objects, O1, and F2 are features that characterize a second set of objects, O2, where F2 is different than F1. In this embodiment, F1 and F2 may have common or related features but there are also different and unrelated features. In this embodiment, object feature mapper 182 assigns a value to the features space of a first set of objects and maps that value to the features space of a different second set of objects. In an example, object feature mapper 182 maps the object to a second set of objects based upon a ranking assigned by ranking model generator 180. Object feature mapper 182 identifies a path and destination for the first set of features in an object to a second object containing a second set of features based upon a similarity score. Given values of features in F1, object feature mapper 182 computes the most similar values in F2 based upon the similarity score. The similarity score is computed from a combination of the similarity metrics, a function that quantifies the similarity between two words, and semantic distances over corresponding concepts in a knowledge database.

Transposer 184 (a sub program of program 200) transposes a ranking model for the first set of objects to a second set of objects. In an embodiment, transposer 184 directs the movement of the ranking model for the first set of objects based upon external feedback, the position in the given ranking of the first set of objects, and the similarity of features values computer by object feature mapper 182. In an example, transposer 184 transposes the new ranking model, generated by using the implicit data derived from ranking model generator 180 for O1, characterized by F1, to construct a ranking model for a different set of objects, O2, characterized by F2.

In one embodiment, program 200 operates on server computer 120. In another embodiment, program 200 operates on another computer in a server based setting; for example, on a server computer not shown. In yet another embodiment, program 200 operates on computing device 110 simultaneously with server computer 120 interconnected through network 185. Program 200 provides the capability to transpose ranking models across two or more sets of objects characterized by different features. Program 200 is capable of utilizing Wi-Fi technology, Bluetooth, Near Field Communication tags (NFC), Global System for Mobile Communications (GSM), and Global Positioning System Technology (GPS) to communicate with computing device 110.

In an example embodiment, program 200 operates as a code snippet within one or more applications on computing device 110. Code snippets define the scope of interactivity between the snippets and the application, (e.g., program 200 hosted by a web browser application on server computer 120). For example, program 200 is a function within web browser 150, and the processes of program 200 occur automatically (i.e., without user intervention) during operation of web browser 150 as initiated by program 200. The dynamic code snippet elements provide scripting support. The variables enable dialog between program 200, through server computer 120, graphical user interface 130, and web browser 150.

Figure 2:
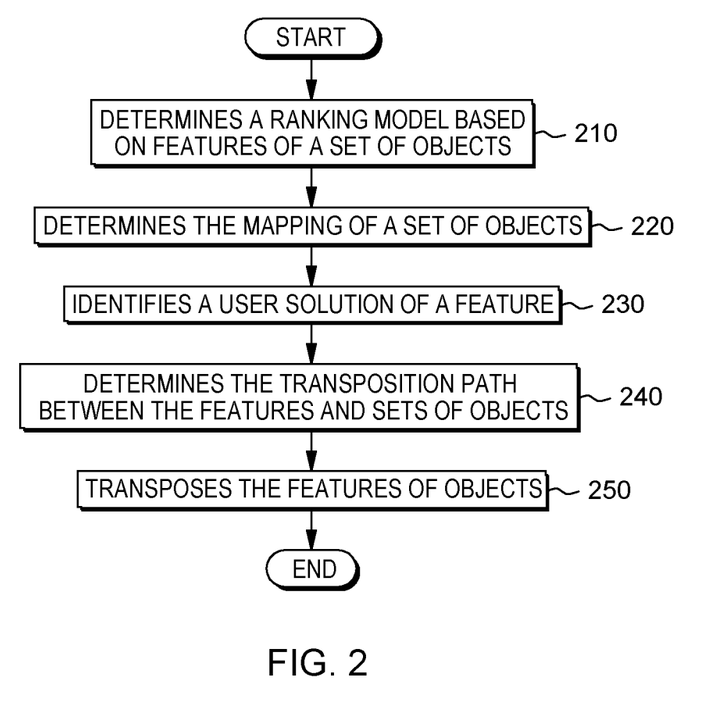
FIG. 2 is a flowchart depicting operational steps of a program for transposing ranking models across two or more sets of objects characterized by different features, in accordance with an embodiment of the present invention.

FIG. 2 is a flowchart depicting the operational steps program 200, a program for transposing ranking models across two or more sets of objects characterized by different features, in accordance with an embodiment of the present invention.

In step 210, program 200 determines a ranking model based on features of a set of objects. In an embodiment, program 200, through sub program ranking model generator 180, determines a baseline ranking model for a record that includes a set of objects based on aspects of the features. In an example, program 200 collects user feedback, analyzes the characteristics of the features, and the history of features in database 170 to determine a ranking model for a first set of objects.

Figure 3A:
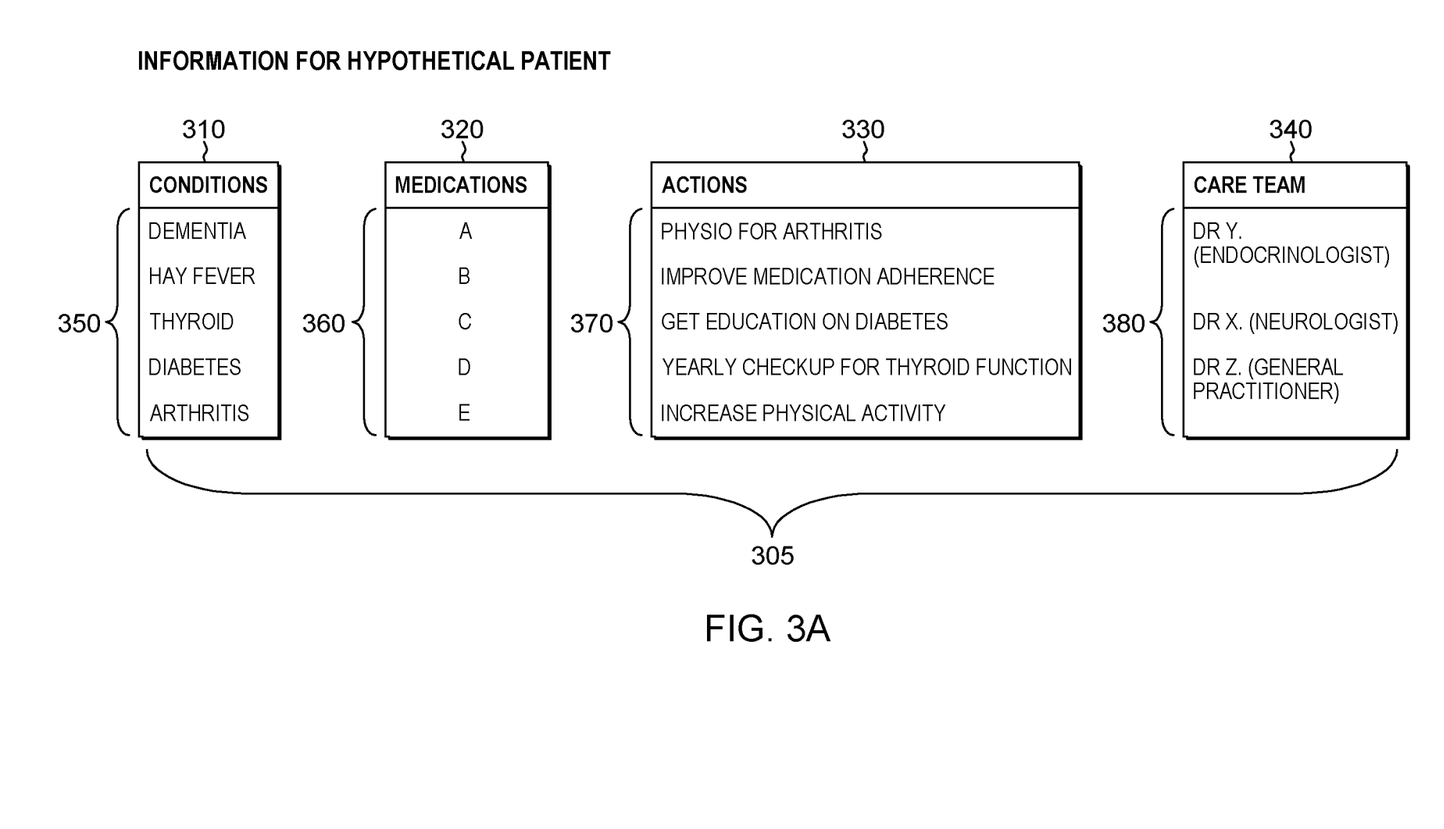
FIG. 3A illustrates an example of program 200 establishing a ranking model, in accordance with an embodiment of the present invention.

FIG. 3A illustrates an example of program 200 establishing a ranking model based on features of a first set of objects, in accordance with an embodiment of the present invention. In this example, with respect to FIG. 3A, program 200 operates on record 305 and displays a hypothetical patient's medical record. The medical record includes object 310, object 320, object 330, and object 340. Each object is characterized by a set of features corresponding to the objects. Program 200 determines that the hypothetical patient's medical record, located on database 170, correlate closely with features of objects 310 and 340. Program 200 consults database 170 and determines that the hypothetical patient has twenty appointments with Dr. Y, an endocrinologist, in the past year. Program 200 consults database 170 and determines that Dr. Y has prescribed actions that are associated with the condition diabetes. Program 200 assigns a high importance rank to Dr. Y, the endocrinologist, and diabetes as a "condition." Program 200 creates a ranking model that suggests the hypothetical patient is likely being treated for diabetes as their prime "condition."

In step 220, program 200 determines the mapping of a set of objects. In an embodiment, program 200, through object feature mapper 182, determines a plurality of relationships between features in a data record. In an example embodiment, the position of features in other objects will change as a result of a change to a ranking value associated with a feature. The ranking of the features of a different set of objects are initially displayed as a function of the ranking model determined in step 210.

The medical record includes object 310, object 320, object 330, and object 340. Each object is characterized by a set of features corresponding to the objects. In the depicted embodiment, based upon the determination that program 200 made in step 210, program 200 connects the features and objects. Program 200 determines that features 350 corresponds to "Conditions" (i.e., object 310), features 360 corresponds to "Medications" (i.e., object 320), features 370 corresponds to "Actions" (i.e., object 330), and features 380 corresponds to "Care Team" (i.e., object 340). For example, program 200 determines that the features 360, of object 320, features 370 of object 330, and features 380 of object 340 are dependent on the characteristics of features 350 of object 310. In this example, based upon an earlier determination, program 200 identifies that features 350 of object 310, "Conditions" (i.e., object 310), direct the process for the other features. "Medications" (i.e. object 320), "Actions"

(i.e., object 330), and "Care Team" (i.e., object 340) are all determined as a function of "Conditions" (i.e., object 310). In this example, program 200 determines the ranking model based upon the fact that a hypothetical patient's condition will determine the type of "medication" a physician assigns the patient (i.e., object 320), the type of "action" that the physician will assign the patient (i.e., object 330), and the "care team" that will be assigned to the patient (i.e., object 340).

Figure 3B:
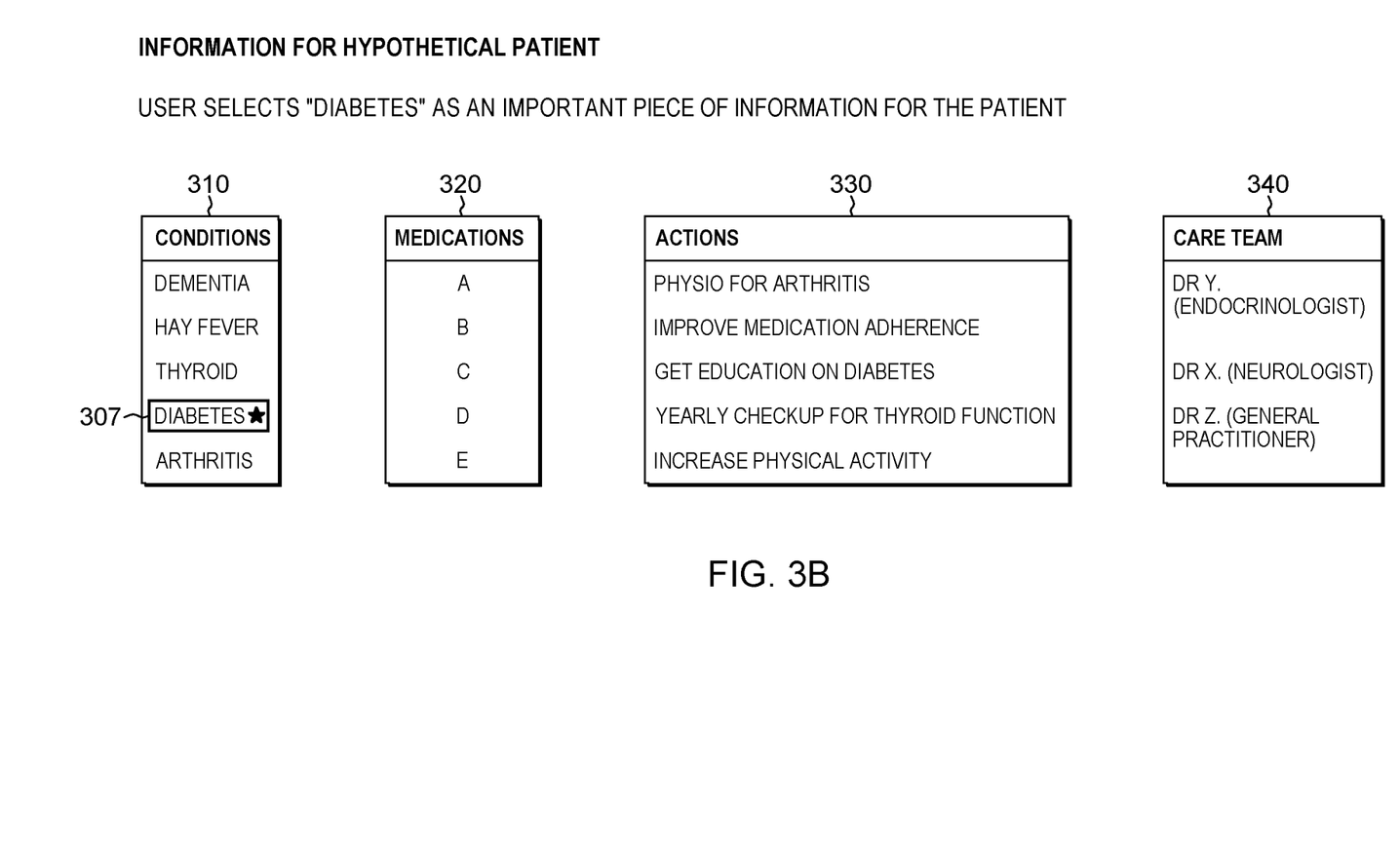
FIG. 3B illustrates an example of program 200 determining the mapping of a second set of objects to a first set of objects, in accordance with an embodiment of the present invention.

FIG. 3B illustrates an example of program 200 determining the relationships between different features within a data record based upon an analysis of the record of a patient and medical knowledge database, in accordance with an embodiment of the present invention.

The medical record includes object 310, object 320, object 330, and object 340. Each object is characterized by a set of features corresponding to the objects. In the depicted embodiment, based upon the determination that program 200 made in step 210, program 200 connects the features and objects. Program 200 determines that features 350 corresponds to "Conditions" (i.e., object 310), features 360 corresponds to "Medications" (i.e., object 320), features 370 corresponds to "Actions" (i.e., object 330), and features 380 corresponds to "Care Team" (i.e., object 340). For example, program 200 determines that the features 360, of object 320, features 370 of object 330, and features 380 of object 340 are dependent on the characteristics of features 350 of object 310. In this example, based upon an earlier determination, program 200 identifies that features 350 of object 310, "Conditions" (i.e., object 310), direct the process for the other features. "Medications A, B, C, D, and E" (i.e., object 320), "Actions" (i.e., object 330), and "Care Team" (i.e., object 340) are all determined as a function of "Conditions" (i.e., object 310). In this example, program 200 determines the ranking model based upon the fact that a hypothetical patient's condition will determine the type of "medication" a physician assigns the patient (i.e., object 320), the type of "action" that the physician will assign the patient (i.e. object 330), and the "care team" that will be assigned to the patient (i.e. object 340).

In this example, program 200 consults a medical knowledge database to determine the features of objects 310, 320, and 330 that are related to diabetes. Program 200 analyzes object 320 and determines that the feature "Medication A" of object 320 is associated with the "Diabetes" feature. Similarly, program 200 determines that the other "medications" listed in object 320 correspond to treatments, based on information retrieved from the data in a medical knowledge database, of the conditions in the record of a patient. In this example, program 200 determines that the features in object 310 are derived from a characterization of the record of a patient. The record presents that the patient has had symptoms or been diagnosed with the conditions in object 310.

In another embodiment, program 200 determines that the medical record of an individual patient contains multiple instances of the patient visiting an Endocrinologist. In this example, program 200 analyzes the totality of the patient's record and identifies other data that correlates to diabetes. In this example, program 200 queries a knowledge resource to identify details of normal health measures, such as blood pressure, heart rate, blood sugar, and body mass index. Program 200 determines that the patient's medical records exhibit values for the health measures that are consistent with the medical condition diabetes. Program 200 is capable of clustering, or associating, the data in a medical record to establish a connection between multiple features.

In step 230, program 200 identifies a user selection of a feature. In an embodiment, program 200 determines that a user has selected a feature (e.g., a user indicating a feature as important). In an example with reference to FIG. 3B, a user selects "Diabetes" 307 as an important feature of object 310. Object 310 is a list that contains different medical conditions. Ranking model generator 180 determines that "Diabetes" 307 is the user selected important feature and assigns a high-preference feature value, in combination with the ranking model established in step 210, to "Diabetes" 307. Ranking model generator 180 also assigns a high ranking to "Diabetes" 307, which program 200 can utilize to determine an updated ranking system for features in record 305.

In an additional example, program 200 identifies a history of user selections as determining that "Diabetes" is the primary condition of the hypothetical patient. Program 200 automatically, without user intervention, identifies "Diabetes" as the feature of importance.

In step 240, program 200 determines the transposition path between the features and sets of objects. In an embodiment, program 200, through sub program transposer 184, transposes the ranking model (determined in step 210) based on the identified user-selected feature (from step 230).

In this example, program 200, as discussed in step 230, identifies that "Diabetes" 307 is important. In a scenario where a value of 5 is the highest value possible, program 200 assigns a value of 5 to "Diabetes" as a feature. Program 200 analyzes objects 310, 320, 330, and 340 to identify features that are related to the "Diabetes" feature, based on the determine mapping of features of the objects (from step 220). Program 200 updates ranking values associated with the features that are related to the "Diabetes" feature based on the assigned ranking value of "5" to the "Diabetes" feature. In another example, program 200 assigns the ranking associated with "Diabetes" 307 to features in objects 310, 320, 330, and 340 that are related to the "Diabetes" feature, based on the determine mapping of features of the objects (from step 220).

Program 200 determines the transposition path based upon the relationship between the features as was determined in step 220. The transposition path is directed based upon the features within the objects being shown to be related, and program 200 identifying that a user has designated a feature as important.

In step 250, program 200 transposes the features of objects. In an embodiment, program 200 transposes the features of included in objects within a data record based on the determination of features as being related from step 220, and program 200 identifying a user selection of an important feature.

Figure 3C:
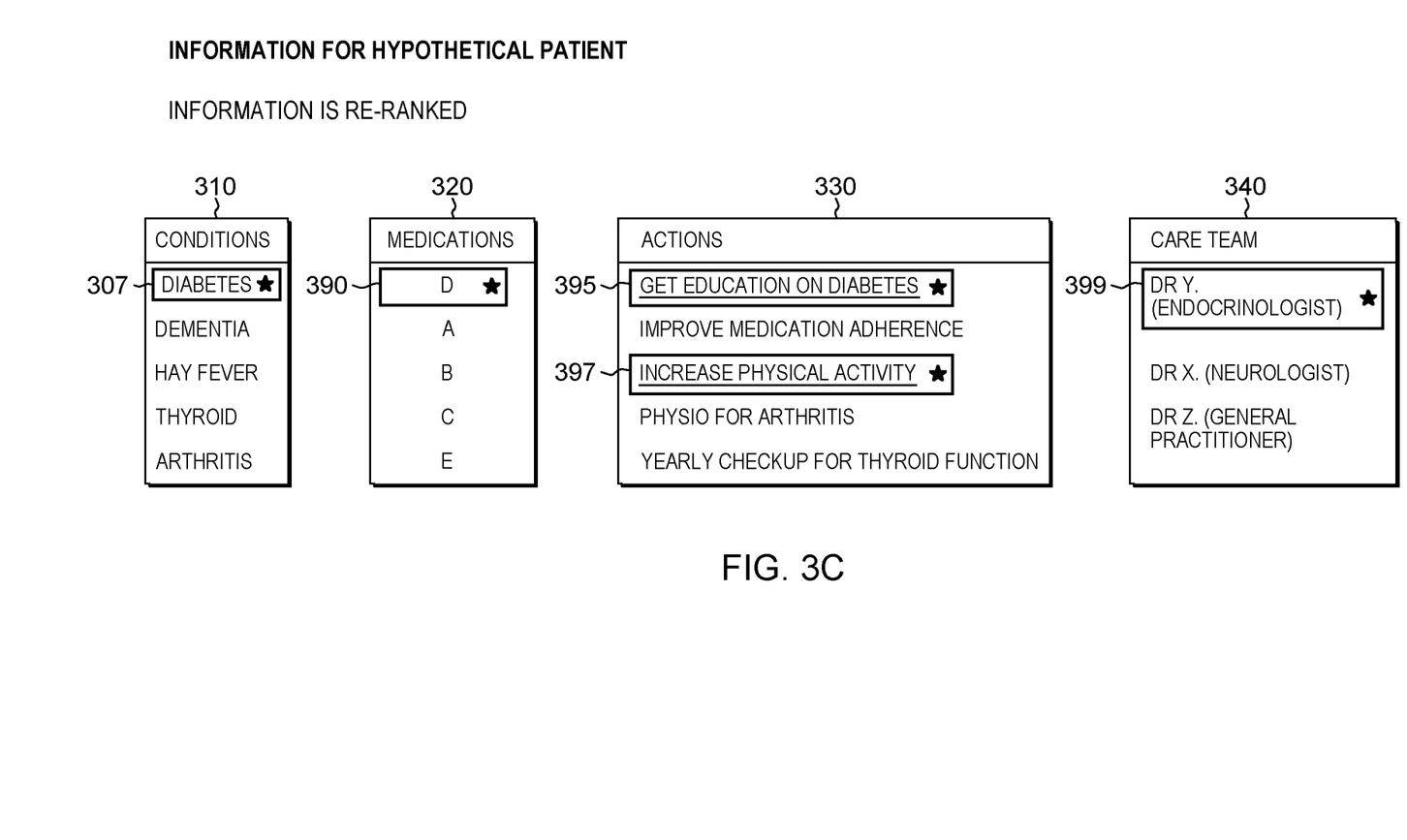
FIG. 3C illustrates an example of program 200 transposing the ranking model across three sets of objects characterized by different features, in accordance with an embodiment of the present invention.

FIG. 3C illustrates an example of program 200 re-ranking the features of the objects as a function of transposition path, in accordance with an embodiment of the present invention. In an embodiment, program 200 determines that object 330 contains similar features, diabetes related, as object 310 and object 320. FIG. 3C illustrates an example of program 200 re-ranking the features of the object 330, that have features related to object 320, as a function of the features of object 310, determined by the ranking model that program 200 created in step 210 and program 200 further corroborating the importance of the feature through identifying a user selection that confirms the importance of "Diabetes" 307, in accordance with an embodiment of the present invention.

In this example with reference to FIG. 3C, program 200 re-ranks "Diabetes" 307 of object 310, and feature "D" 390 of object 320. Program 200, through transposer 184, utilizes external feedback from a knowledge database, and database 170, to transpose the ranking of features of object 310 to rankings associated with features of objects 320, as a function of the transposition path determined by program 200. Program 200, through transposer 184, also transposes the ranking of a feature as a function of the determined transposition path from step 240, utilizing the position in the given ranking of the first set of objects. Program 200 accesses object feature mapper 182 to utilize the similarity of feature values (determined in step 220) to transpose the ranking for object 310 to a ranking of object 320.

In the example depicted in FIG. 3C, "Diabetes" 307 is ranked at the top of object 310. As identified in step 230, "Diabetes" is assigned an elevated priority relative to the other features in objects 310. Program 200 determines a transposition path resulting in assigning the features related to "Diabetes" the highest position among a set of objects to denote the importance of the features. In the depicted example, feature "D" 390 is now ranked highest because "Medication D" is typically described as a medication for "Diabetes."

In this example, program 200 analyzes objects 310 and 330 and determines that the features 395 and 397 of object 330, "Get Education on Diabetes" and "Increase Physical Activity" are also associated with "Diabetes." Program 200, through transposer 184 as determined by the transposition path in step 240, directs the updating process to include features 395 and 397, "Get Education on Diabetes" and "Increase Physical Activity," to the highest and third highest position in the set of objects. Program 200 determines that "Get Education on Diabetes" and "Increase Physical Activity" are related to "Diabetes," analyzing the co-occurrences of the two words in the medical knowledge resource (e.g., in step 220). Program 200 also ranks "Get Education on Diabetes" (i.e., feature 395) highest, and program 200 ranks "Increase Physical Activity" (i.e., feature 397) as the third highest feature of object 330. Program 200 recognizes that both features are related to diabetes, as determined in step 220, based on the co-occurrence in the literature, but program 200 determines, through accessing medical knowledge resource databases, that "Increase Physical Activity" (i.e., feature 397) is a general action that is applicable to multiple prescription actions.

Program 200 analyzes object 340 and determines that the feature 399 "Dr. Y Endocrinologist", of object 340, is associated with "Diabetes." Program 200 further determines that feature 399 was already at the highest position of the list, having the highest ranking and priority as being related to "Diabetes", so the result does not change. The set of features in object 340 are not changed despite transposer 184 transposing the features from the related features as initially determined in step 220.

Figure 4:
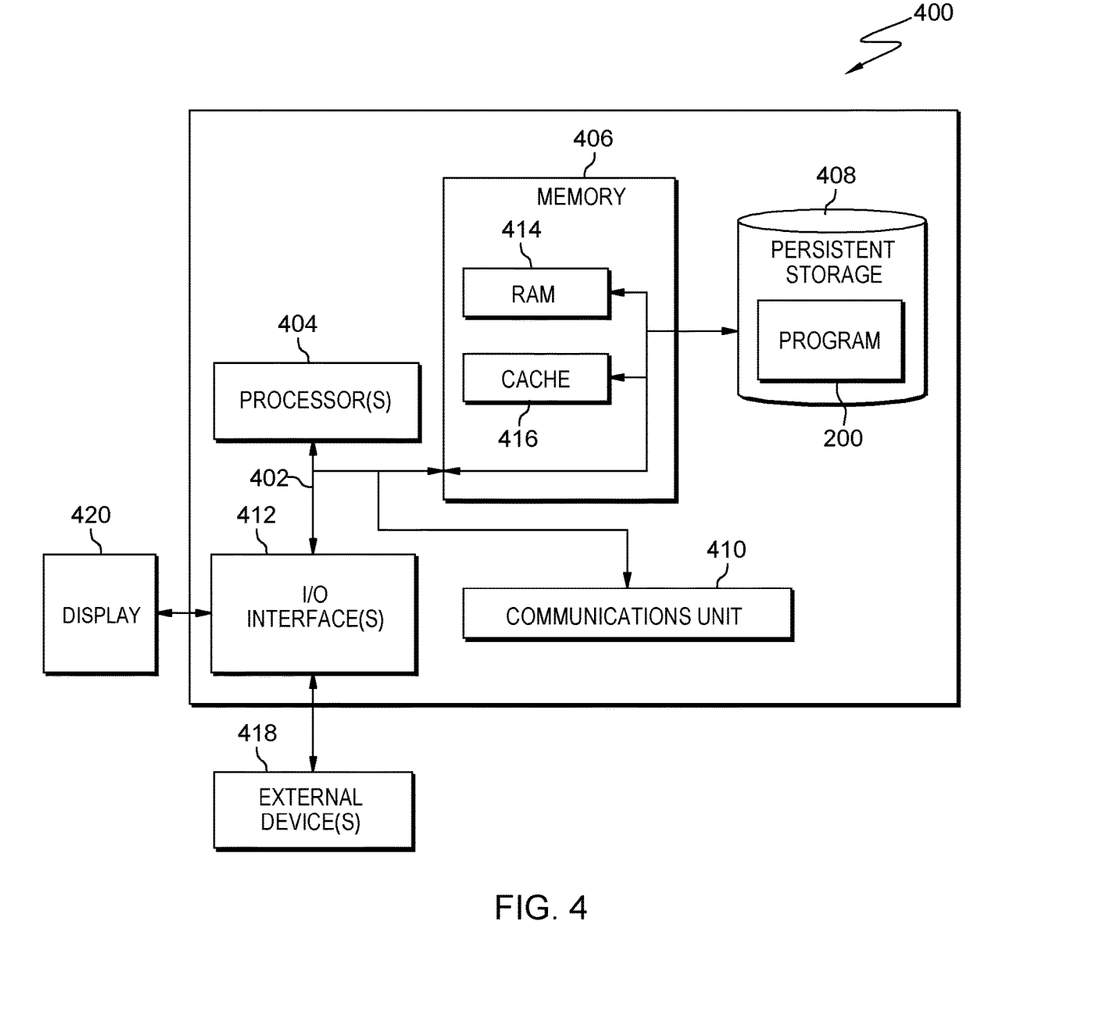
FIG. 4 is a block diagram of components of a computer system, such as the server computer of FIG. 1, in accordance with an embodiment of the present invention.

FIG. 4 depicts a block diagram of components of server computer 120, in accordance with an illustrative embodiment of the present invention. It should be appreciated that FIG. 4 provides only an illustration of one implementation and does not imply any limitations with regard to the environments in which different embodiments may be implemented. Many modifications to the depicted environment may be made.

Server computer 120 includes communications fabric 402, which provides communications between cache 416, memory 406, persistent storage 408, communications unit 410, and input/output (I/O) interface(s) 412. Communications fabric 402 can be implemented with any architecture designed for passing data and/or control information between processors (such as microprocessors, communications and network processors, etc.), system memory, peripheral devices, and any other hardware components within a system. For example, communications fabric 402 can be implemented with one or more buses or a crossbar switch.

Memory 406 and persistent storage 408 are computer readable storage media. In this embodiment, memory 406 includes random access memory (RAM) 414. In general, memory 406 can include any suitable volatile or non-volatile computer readable storage media. Cache 416 is a fast memory that enhances the performance of computer processor(s) 404 by holding recently accessed data, and data near accessed data, from memory 406.

Program 200 may be stored in persistent storage 408 and in memory 406 for execution by one or more of the respective computer processors 404 via cache 416. In an embodiment, persistent storage 408 includes a magnetic hard disk drive. Alternatively, or in addition to a magnetic hard disk drive, persistent storage 408 can include a solid state hard drive, a semiconductor storage device, read-only memory (ROM), erasable programmable read-only memory (EPROM), flash memory, or any other computer readable storage media that is capable of storing program instructions or digital information.

The media used by persistent storage 408 may also be removable. For example, a removable hard drive may be used for persistent storage 408. Other examples include optical and magnetic disks, thumb drives, and smart cards that are inserted into a drive for transfer onto another computer readable storage medium that is also part of persistent storage 408.

Communications unit 410, in these examples, provides for communications with other data processing systems or devices. In these examples, communications unit 410 includes one or more network interface cards. Communications unit 410 may provide communications through the use of either or both physical and wireless communications links. Whitelist update program 200 may be downloaded to persistent storage 408 through communications unit 410.

I/O interface(s) 412 allows for input and output of data with other devices that may be connected to server computer 120. For example, I/O interface 412 may provide a connection to external devices 418 such as a keyboard, keypad, a touch screen, and/or some other suitable input device. External devices 418 can also include portable computer readable storage media such as, for example, thumb drives, portable optical or magnetic disks, and memory cards. Software and data used to practice embodiments of the present invention, e.g., program 200, can be stored on such portable computer readable storage media and can be loaded onto persistent storage 408 via I/O interface(s) 412. I/O interface(s) 412 also connect to a display 420. Display 420 provides a mechanism to display data to a user and may be, for example, a computer monitor.

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punchcards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The descriptions of the various embodiments of the present invention have been presented for purposes of illustration, but are not intended to be exhaustive or limited to the embodiments disclosed. Many modifications and variations will be apparent to those of ordinary skill in the art without departing from the scope and spirit of the invention. The terminology used herein was chosen to best explain the principles of the embodiment, the practical application or technical improvement over technologies found in the marketplace, or to enable others of ordinary skill in the art to understand the embodiments disclosed herein.

What is claimed is:

1. A method for transposing ranking models, the method comprising:
   determining, by one or more processors, an initial ranking modeling framework for a record based on analyzing data from a plurality of objects within the record, wherein an object includes at least one feature;
   determining, by one or more processors, a mapping of relationships between features included in the record, including:
      determining, by one or more processors, a value for the strength of association of a word in a first feature with one or more features co-occurring in a knowledge database,
      generating, by one or more processors, a similarity score for the first feature in the record relative to a second feature in the record based upon the value for the strength of association of the word in the first feature in combination with the co-occurrence of the first feature and the second feature in a knowledge database, and
      applying, by one or more processors, the similarity score for the second feature relative to the first feature;
   identifying, by one or more processors, a user selection of a feature;
   determining, by one or more processors, a transposition path between the user selected feature and a set of features that have a determined mapped relationship to the user selected feature;
   modifying, by one or more processors, ranking information associated with features included in the determined transposition path;
   reordering, by one or more processors, the set of features included in the record based on the modified ranking information; and
   displaying, by one or more processors, the reordered set of features on a computer device.

2. The method of claim 1, wherein determining a transposition path between the user selected feature and a set of features that have a determined mapped relationship to the user selected feature further comprises:
   assigning, by one or more processors, a similarity score to one or more features based upon an identified user selection of a feature; and
   determining, by one or more processors, a reordering of features based upon the identified user selection of a feature in an object.

3. The method of claim 1 wherein reordering the record further comprises:
   changing, by one or more processors, the positioning of features within respective objects of the record based on the modified ranking information.

4. The method of claim 1 wherein an initial ranking modeling framework is a baseline determination and display constructed using implicit knowledge derived from a history of the features in a database.

5. The method of claim 3, wherein reordering the record further comprises:
   updating, by one or more processors, the positioning of features as a function of integrating a previously constructed ranking model built for other objects.

6. A computer program product for transposing ranking models, the computer program product comprising:
   one or more computer readable tangible storage media and program instructions stored on at least one of the one or more computer readable storage media, the program instructions readable/executable by one or more computer processors and further comprising:
   program instructions to determine an initial ranking modeling framework for a record based on analyzing data from a plurality of objects within the record, wherein an object includes at least one feature;
   program instructions to determine a mapping of relationships between features included in the record, including
      program instructions to determine a value for the strength of association of a word in a first feature with one or more features co-occurring in a knowledge database,
      program instructions to generate a similarity score for the first feature in the record relative to a second feature in the record based upon the value for the strength of association of the word in the first feature in combination with the co-occurrence of the first feature and the second feature in a knowledge database, and
      program instructions to apply the similarity score for the second feature relative to the first feature;
   program instructions to identify a user selection of a feature;
   program instructions to determine a transposition path between the user selected feature and a set of features that have a determined mapped relationship to the user selected feature;
   program instructions to modify ranking information associated with features included in the determined transposition path;
   program instructions to reorder the set of features included in the record based on the modified ranking information; and
   program instructions to display the reordered set of features on a computer device.

7. The computer program product of claim 6, wherein the program instructions to determine a transposition path between the user selected feature and a set of features that have a determined mapped relationship to the user selected feature, further comprises program instructions to:
   assign a similarity score to one or more features based upon an identified user selection of a feature; and
   determine a reordering of features based upon the identified user selection of a feature in an object.

8. The computer program product of claim 6, wherein the program instructions to reorder the record, further comprises program instructions to:
   change the positioning of features within respective objects of the record based on the modified ranking information.

9. The computer program product of claim 6, wherein an initial ranking modeling is a baseline determination and display constructed using implicit knowledge derived from a history of the features in a database.

10. The computer program product of claim 8, wherein reordering the record further comprises program instructions to:
    update the positioning of features as a function of integrating a previously constructed ranking model built for other objects.

11. A computer system for transposing ranking models, the computer system comprising:
    one or more computer processors;
    one or more computer readable storage media; and program instructions stored on the computer readable storage media for execution by at least one of the one or more computer processors, the program instructions comprising:

program instructions to determine an initial ranking modeling framework for a record based on analyzing data from a plurality of objects within the record, wherein an object includes at least one feature;

program instructions to determine a mapping of relationships between features included in the record, including program instructions to determine a value for the strength of association of a word in a first feature with one or more features co-occurring in a knowledge database, program instructions to generate a similarity score for the first feature in the record relative to a second feature in the record based upon the value for the strength of association of the word in the first feature in combination with the co-occurrence of the first feature and the second feature in a knowledge database, and program instructions to apply the similarity score for the second feature relative to the first feature;

program instructions to identify a user selection of a feature;

program instructions to determine a transposition path between the user selected feature and a set of features that have a determined mapped relationship to the user selected feature;

program instructions to modify ranking information associated with features included in the determined transposition path;

program instructions to reorder the set of features included in the record based on the modified ranking information; and program instructions to display the reordered set of features on a computer device.

12. The computer system of claim 11, wherein the program instructions to determine a transposition path between the user selected feature and a set of features that have a determined mapped relationship to the user selected feature, further comprises program instructions to:

assign a similarity score to one or more features based upon an identified user selection of a feature; and determine a reordering of features based upon the identified user selection of a feature in an object.

13. The computer system of claim 11, wherein the program instructions to reorder the record, further comprises program instructions to:

change the positioning of features within respective objects of the record based on the modified ranking information.

14. The computer system of claim 11, wherein an initial ranking modeling is a baseline determination and display constructed using implicit knowledge derived from a history of the features in a database.

* * * * *